United States Patent [19]

Slanetz, Jr.

[11] Patent Number: 4,469,091
[45] Date of Patent: Sep. 4, 1984

[54] TACTILE CONTROL DEVICE FOR A REMOTE SENSING DEVICE

[76] Inventor: Charles A. Slanetz, Jr., 10 Tayer Rd., Locust Valley, N.Y. 11560

[21] Appl. No.: 416,259

[22] Filed: Sep. 9, 1982

Related U.S. Application Data

[62] Division of Ser. No. 182,071, Aug. 28, 1980, Pat. No. 4,366,810.

[51] Int. Cl.³ .............................................. A61B 1/06
[52] U.S. Cl. .......................................................... 128/6
[58] Field of Search .................................. 128/3–8, 128/DIG. 9, 348, 772; 200/61.13, 61.41, 61.42, 73, 18; 307/115, 119, 113; 318/578, 670, 671; 356/241; 254/134.3 FT; 340/573, 686, 128

[56] References Cited

U.S. PATENT DOCUMENTS

| | | | |
|---|---|---|---|
| 3,355,811 | 12/1967 | Tailleur | 200/61.42 |
| 3,509,360 | 4/1978 | Miller | 307/119 |
| 4,159,429 | 6/1979 | Migliardi et al. | 200/61.42 X |
| 4,273,111 | 6/1981 | Tsukaya | 128/6 |
| 4,286,585 | 9/1981 | Ogawa | 128/6 |

Primary Examiner—Mickey Yu
Attorney, Agent, or Firm—Kenyon & Kenyon

[57] ABSTRACT

The remote sensing device is added to a fibro-optic illuminating and viewing system such as a colonoscope. The directional sensing device is located in a flexible hood surrounding the distal end of the fiberscope. The sensor devices located in the hood at close spacings consist of semi-conductive digital foam sheath with electrodes located on its inside surface. The sheath and electrodes are attached to an ohmmeter so that when the instrument contacts with the wall, e.g. of a colon, the pressure is measured. The completed circuit forms a signal which is used to direct the distal end of the fiberscope in a direction away from the point of greatest resistance so as to follow the lumen with greater safety.

Contacts may also be positioned along the length of the endoscope so as to be activated by tension below the level of pressure required to disrupt the intestinal wall, or when used in other applications, at a level of pressure appropriate to that use.

20 Claims, 7 Drawing Figures

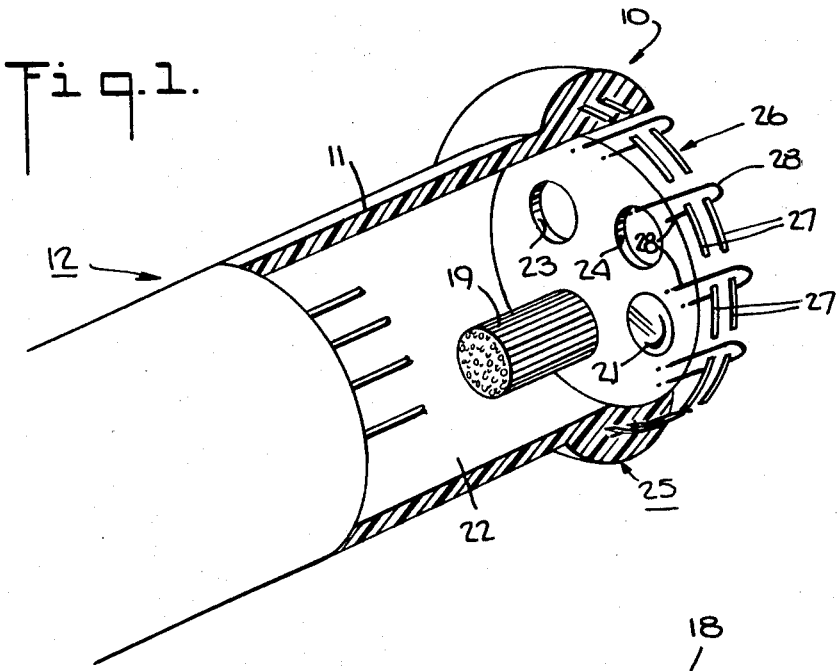
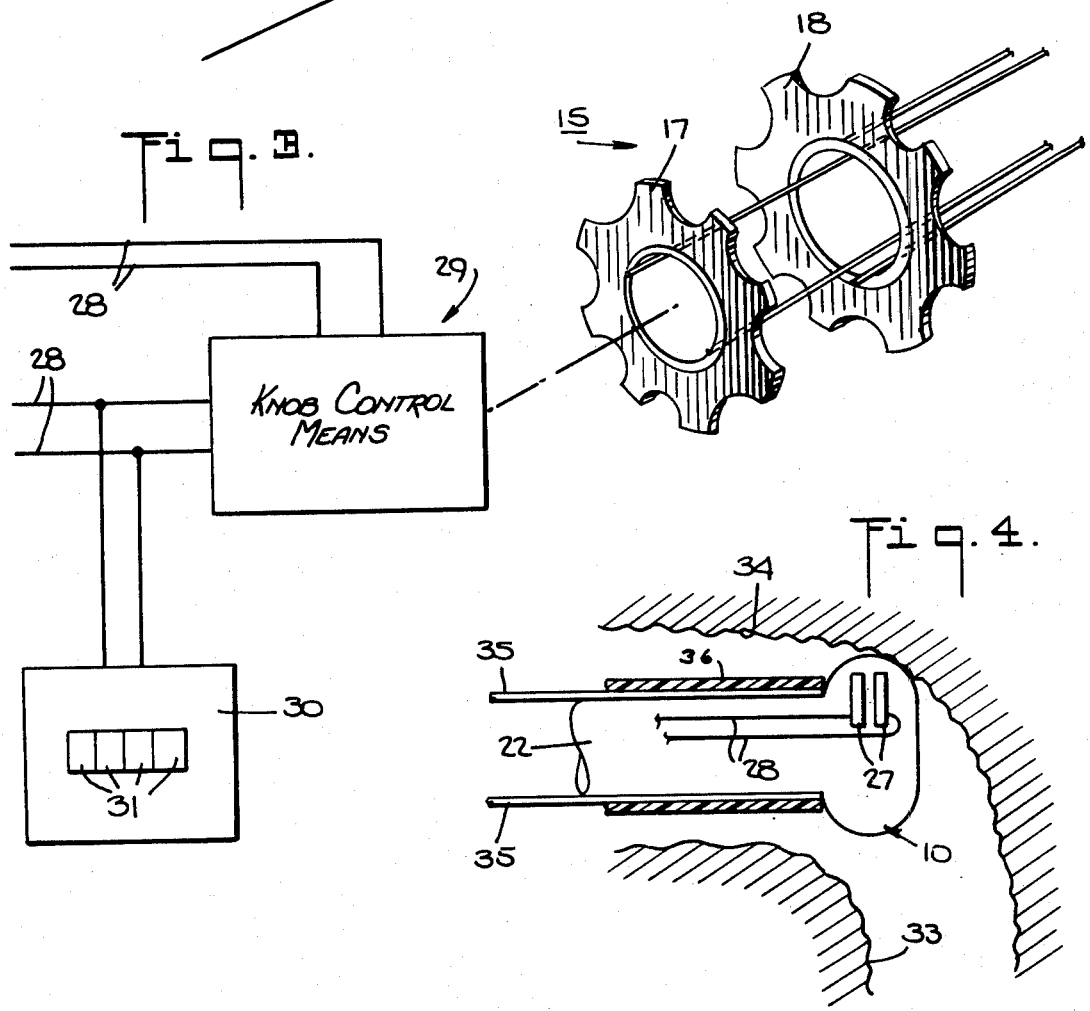

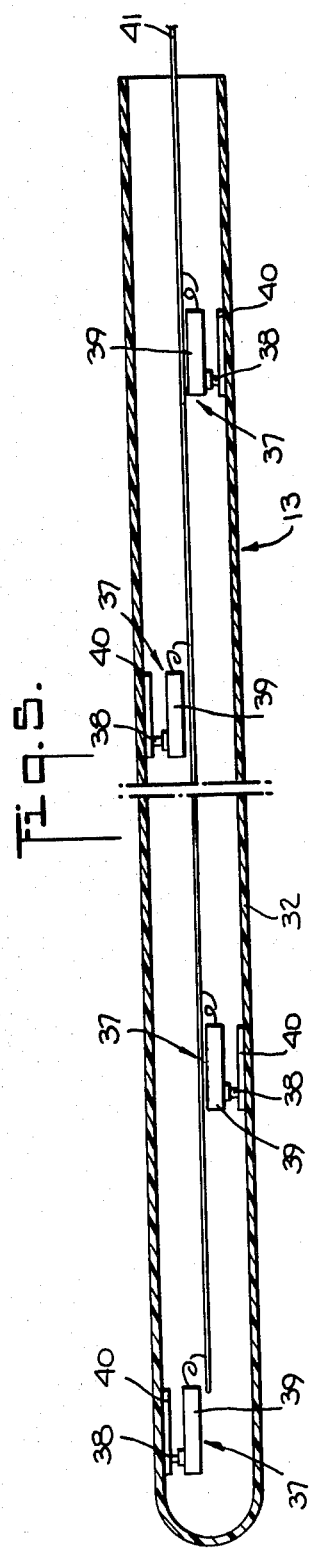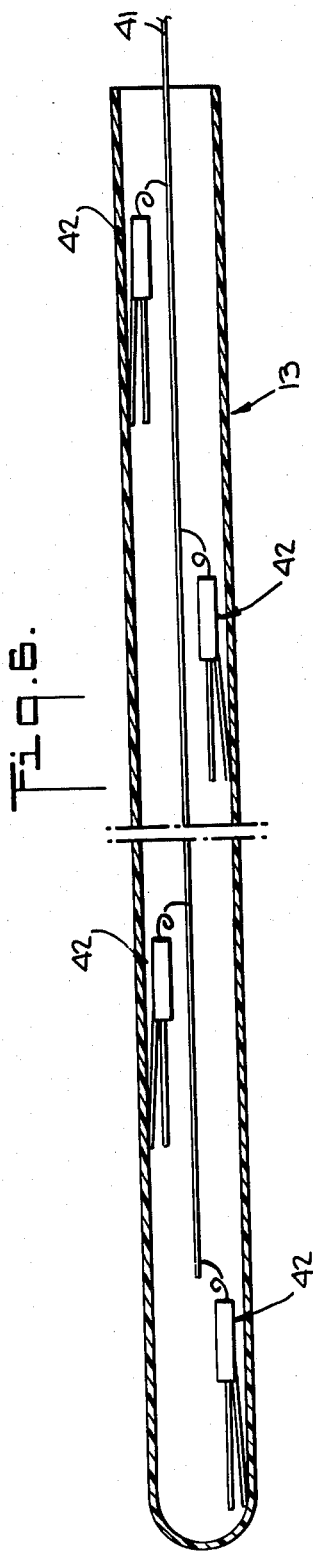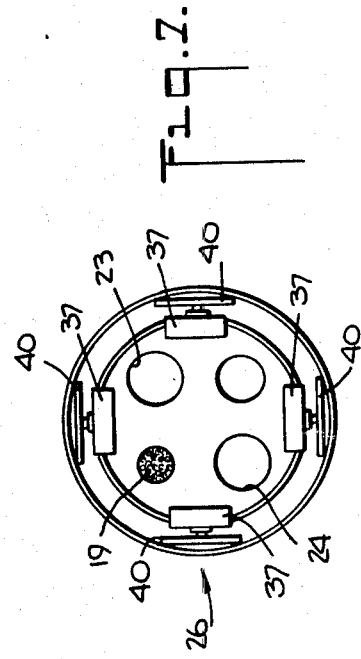

TACTILE CONTROL DEVICE FOR A REMOTE SENSING DEVICE

This is a division of application Ser. No. 182,071 filed Aug. 28, 1980 now U.S. Pat. No. 4,366,810.

The invention relates to a tactile control device. More particularly, this invention relates to a tactile control device which is used as a remote sensing device for a fiberscope.

In many cases, it has been desirable to examine internal organs, passages and the like of the human body for purposes of diagnosis, biopsy, and polyp removal in preparation for surgery without cutting open the patient. An examination of intestine prior to surgery can enable a surgeon to better prepare for what he encounters at operation. The benefits of a prior visual examination without surgery are obvious. One method of examining the internal organs of the patient without major surgery is to insert a remote sensing device such as a fibroptic endoscope into the body through a natural body orifice or a specially prepared surgical opening.

The use of remote sensing devices for internal examination is not limited to medicine. Remote sensing devices can be used to examine the interior of otherwise inaccessible mechanical structures without opening them; such as aircraft wings, the walls of buildings, the enclosed areas of any structure. In these cases, an internal examination, without putting a major opening in the structure, can help to determine the reason for mechanical failure or the level of corrosion levels.

When using a remote sensing device, a common problem arising in medical or mechanical applications is to be able to maneuver the inspection end of the device around obstructions to the proximity of the area of interest. In the past, this maneuvering has been by a trained operator who will see the obstruction and then hazard a guess as how to direct the device safely around the obstruction. Such a mode of operation without the benefit of binocular depth perception is time consuming. Particularly undesirable in medical observation, is that the prolonged presence of the remote sensing device in the body and the frequent occurrence of excessive pressure of contact on an internal organ can result in damage or perforation at sites most often along the course of the instrument in no way related to the visualized area. In more recent times, use has been made of fiberscopes which allow viewing around bends. These fiberscopes are generally constructed with an elongated flexible insertion tube having a distal end in which an illuminating and viewing system is mounted and a proximal end in which a control unit is mounted for controlling the bending of the tube at the distal end. In many cases, the control unit employs four control cables and two turning knobs to direct the distal end in any one of four directions, i.e., up, down and side-to-side. The illuminating and viewing system usually employs glass fiber optic devices to transmit light to the distal end while allowing viewing of the surrounding environment at the distal end. To this end, the control unit is usually connected to a source of light and carries an eyepiece for viewing purposes.

Generally, when using a fiberscope of the above type, for example for inspection of a colon, the distal end is inserted into a patient via the rectum and is then guided through the colon. In order to direct the distal end and the trailing flexible tube through the colon, the user views through the eyepiece in the control unit. Should the colon turn, the user manipulates the turning knobs of the control unit to bend the distal end up, down, left or right so as to follow the bend of the colon.

However, since the colon follows a tortuous path, the walls of the colon can fold over so as to define bends of 90° or more. In cases where a distal end of a fiberscope reaches such a bend, a "red out" condition is presented. That is, the distal end abuts against the colon wall so that the user cannot see the direction in which the colon is bent. As a result, the user must then withdraw the tube inflate further with air or carbon dioxide and experiment with the turning knobs to determine which direction is the correct one to follow. In some cases, aggravated bendings of the distal end of a fiberscope may tear or otherwise damage the colon wall. In still other cases, use is made of expensive external equipment to determine the direction in which the distal end should be directed.

Accordingly, it is an object of the invention to provide a remote sensing device which can be relatively easily maneuvered around obstructions.

It is another object of the invention to provide a remote sensing device to ease medical examination of internal organs through natural body orifices.

It is another object of the invention to determine that the pressure of the instrument against the wall of an organ in no area exceeds the tensile strength of that organ.

It is another object of the invention to provide a remote sensing device for internal examination that will automatically provide data to detect obstructions and provide information for avoiding the obstruction.

It is another object of the invention to provide a tactile control device which can be incorporated into existing fiberscopes.

Briefly, the invention provides a tactile control device which comprises a flexible hood, made for example of a flexible digital foam, for circumferentially surrounding a distal end of a flexible tube of a fiberscope and a plurality of pressure-sensitive sensing devices which are mounted inside the hood for emitting a directional signal in response to pressure from flexing of the hood. In addition, a plurality of contact points can be located along the course of the fiberscope inside a pressure-sensitive covering to prevent lateral torque of the colonoscope from causing, for example, a lateral rupture of the wall of a bowel.

The tactile control device is particularly adapted to function with a fiberscope. For example, the tactile control device may be used with a fiberscope including an elongated flexible insertion tube, an illuminating and viewing system mounted at a distal end of the tube and a control unit for bending the tube at the distal end in two planes. In this case, the flexible directional sending hood is mounted over the distal end so as to circumferentially surround the illuminating and viewing system. In addition, the hood is disposed to project forwardly of the distal end so that the sensing devices are disposed circumferentially forward of the distal end. Upon an inward flexing of the hood, the sensing devices are able to emit a signal indicative of the location of the flexed section of the hood. These signals, in turn, can be used to activate the control unit of the fiberscope in order to direct the distal end in a direction away from the area of greatest pressure.

The sensing units consist of inside contact points with wires running along the instrument inside the pressure sensitive covering, for example a digital foam layer, to an ohmmeter warning system located proximally. The warning system, in turn, has a resistance measuring device, such as an ohmmeter, connected to the contact points to receive the signal and translate the signal into a pressure signal via an ohmmeter measurement. The contact points beneath the flexible hood in the distal portion are directionally oriented to provide the operator with information as to the location of the lumen.

In another embodiment, each sensing device includes a pair of electrically conductive plates, such as piezoelectric crystals, microspring sensors or flexible conductive plastic sandwiches which are disposed in slightly spaced relation to each other and a pair of contact wires. Each wire extends from a respective contact plate so that, when pressure is applied against the wall of the intestine, the plates contact each other and complete an electrical circuit through the wires in order to emit a signal.

In an automatic system, a control means is connected to each pair of wires as well as to the control unit of the fiberscope in order to activate the control unit in response to a received signal. This control is so connected with the sensing devices as to activate the control unit of the fiberscope to bend the distal end in a direction away from the sensing device which causes the signal.

In addition, the tactile control device may employ a display board with indicators to indicate the position of a flexed hood section, i.e. the sensing device causing a signal relative to the remainder of the hood. In this case, the indicators on the display board are suitably connected to the control means or to the pairs of wires leading from the plates in the hood.

When in use, for example, as in a colonoscope, should the distal end of the flexible hood of the tactile control device abut against the bend in a colon, a sensing device will close and emit a responsive signal. The user may then manually adjust the fiberscope via the control unit so as to move the distal end away from the obstruction. Alternatively, the signal may be processed automatically by the control means such that the control unit of the fiberscope automatically responds to the signal to move the distal end away from the obstruction. In this way, the distal end can be maintained in a centered position within the colon passageway even if tortuous bends are encountered in the colon passageway. In essence, the tactile control device augments the illuminating and viewing system of the fiberscope by providing a tactile sense to guide the colonoscope through the colon.

The tactile control device may also have application in industry in directing wires through conduits; in inspecting parts, for example in airplane wings that require internal inspection; detecting openings within walls; and the placement of electrical cables and telephone wires within existing structures in which direct visualization is not possible.

The tactile control device may also be modified to enhance the use of a fiberscope. For example, the control device may include a plurality of pressure-sensitive flexible contacts or switches which can be disposed along the entire length of a fiberscope. Such pressure sensitive covering would respond to predetermined contact pressures thereon, for example the pressures exerted by the wall of the colon. Thus, should the pressure along any portion of the fiberscope exceed the tensile strength, e.g. of a colon wall, the sensors would give a warning of this impending condition.

The pressure sensitive devices which are used both in the tactile control device at the distal end of the fiberscope as well as along the length of the fiberscope may be of the same type with those at the distal end being set for greater sensitivity than those along the length of the fiberscope.

Further, any suitable type of pressure sensitive device may be used including those with variable conductivity, such as Dynacon A, B, C or D as described in "Computer Magazine", March 1978 issue, under the title "Digital Foam".

These and other objects and advantages of the invention will become more apparent from the following detailed description taken in conjunction with the drawings in which:

FIG. 1 illustrates a schematic view of a tactile control device on the distal end of a fiberscope in accordance with the invention;

FIG. 3 illustrates a schematic view of a system utilizing a tactile control device according to the invention;

FIG. 4 illustrates a view of the tactile control device at a bend within a colon;

FIG. 5 illustrates a partial cross-sectional view of flexible tube of a fiberscope with pressure sensitive switches disposed along the length thereof;

FIG. 6 illustrates a partial cross-sectional view of a fiberscope utilizing another form of pressure sensitive switch; and FIG. 7 illustrates an end view of a modified tactile control device for a fiberscope in accordance with the invention.

Figure 2:
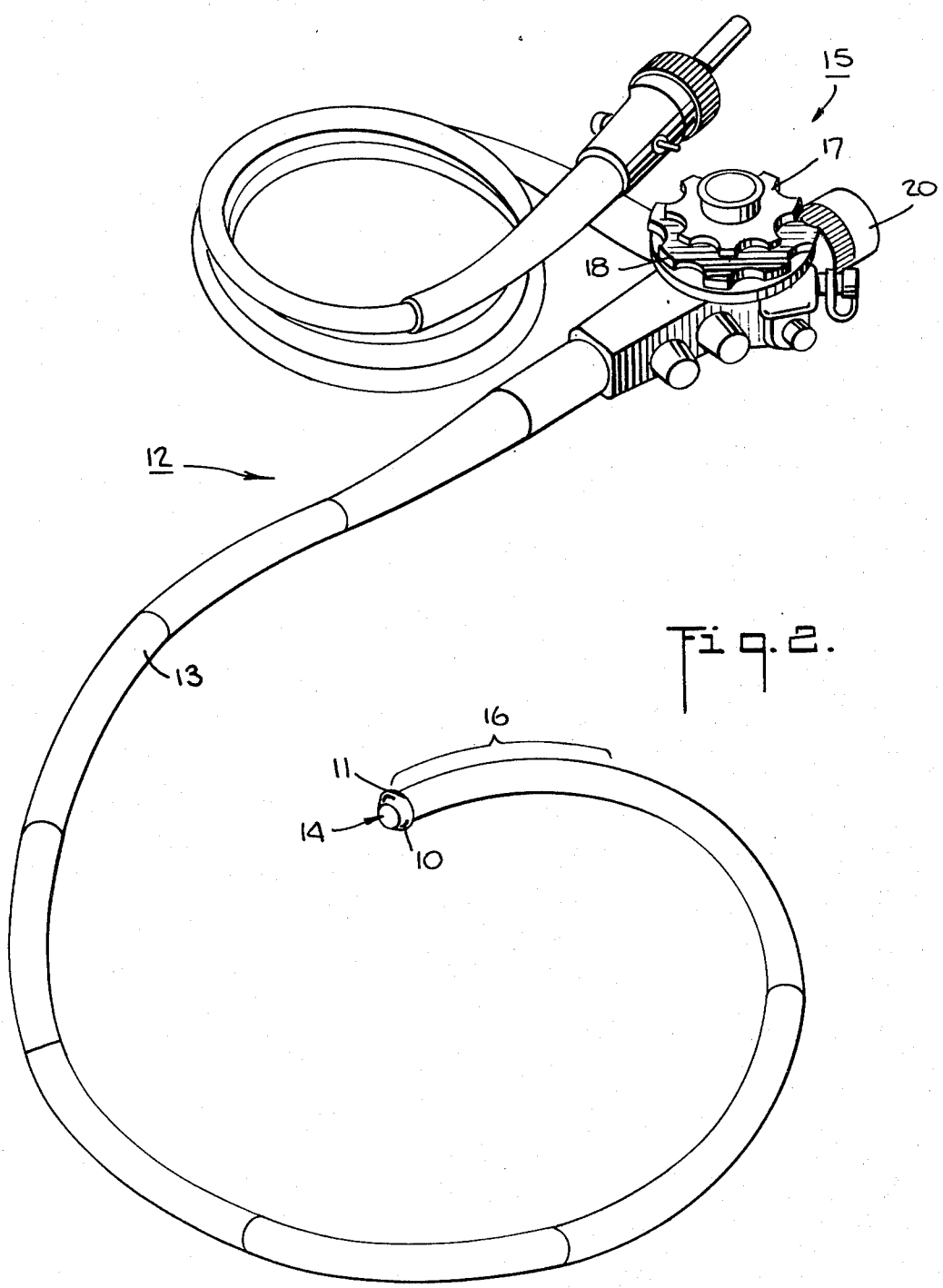
FIG. 2 illustrates a view of the fiberscope of FIG. 1 with the tactile control device removed.

Referring to FIG. 1, the directional tactile control device 10 is adapted for mounting on the distal end 11 of a fiberscope 12, for example a colonoscope. In this regard, the fiberscope can be made of any suitable construction adapted for entry into other anatomical passages than the colon. Such fiberscopes are of known construction and need not be described in detail.

Alternatively, the fiberscope can be of a construction which can be employed in industrial applications, such as to inspect lines in an airplane wing.

Referring to FIG. 2, the fiberscope 12 includes an elongated flexible insertion tube 13 which terminates at the distal end 11, an illuminating and viewing system 14 mounted at the distal end 11 and a control unit 15 at the proximal end of the tube 13 for bending the tube 13 at the distal end in two planes. For example, the control unit 15 employs two pairs of cables (not shown) which extend to a bending section 16 of the tube 13 as well as two knobs 17, 18 which function to control the cables so as to affect movement of the bending section 16 in one of four directions, namely up, down, and from side-to-side. The illuminating and viewing system 14 employs a flexible optic fiber bundle 19 (FIG. 1) which extends from the distal end 11 to the control unit 15. The control unit 15 can be connected to a suitable illuminating means (not shown) which has a light source for transmitting light through at least one of the optic fibers to illuminate an object of interest at the distal end 11 of the tube 13. In addition, a viewing means 20 such as an eye-piece or a camera (not shown) is mounted on the control unit 15 to permit viewing of the object of interest via a lens 21 at the distal end 11.

Referring to FIG. 1, the fiberscope 12 has a flexible central shaft 22, e.g. of Teflon which houses the fiber bundle 19 and lens 21. In addition, the shaft 22 has a pair of passageways 23, 24 which serve for the usual purposes, for example for inflating and suction procedures, for biopsy, or other tissue collecting procedures.

The tube 13 of the fiberscope 12 is sized to be passed through a colon and has sufficient flexibility so as to bend during passage through a colon passageway. The flexible tube 13 has a circular cross-section and acts as a conductor of visual and electrical information between the object under examination and the operator. To this end, the bundle of optical fibers 19 transmit light to the distal end 11 in order to illuminate the object under examination, while reflected light is passed through the lens 21 to the eye-piece 20 for visual examination. Alternatively, or in addition, a camera can be connected to the eyepiece in order to take still pictures or motion pictures. Also, the image received at the eye-piece may be transmitted to a television monitor or the like for viewing by others.

Referring to FIG. 1, the tactile control device 10 includes a flexible hood 25, e.g. of flexible digital foam, such as Dynacon, which circumferentially surrounds the illuminating and viewing system 14 at the distal end 11 of the fiberscope 12. As shown, the hood 25 projects forwardly of the distal end 11, for example a distance of one centimeter, and is made in the shape of a ball of flexible material, such as a clear flexible ethlion. In addition, the tactile control device 10 includes a plurality of sensing devices 26 which are disposed circumferentially on the hood 25 forward of the distal end 11 to cover the inside surface of the hood 25. Each sensing device 26 is responsive to an inward flexing of a section of the hood 25 in order to emit a signal indicative of the location of the flexed hood section. To this end, each sensing device 26 includes a pair of electrically conductive plates 27 which are disposed in slightly spaced relation to each other, for example, at a distance of three millimeters, and a pair of contact wires 28 which are connected to the plates 27. These contact wires 28 extend from the plates 27 to a suitable control means 29 (FIG. 3). As shown, the contact plates 27 are of elongated construction and are formed, for example of piezoelectric crystals or microspring sensors. The spacing apart of the plates 27 and the flexibility of the hood 25 are such that the plates 27 of a sensing means 26 contact each other upon inward flexing of the hood 25 when the hood abuts against the wall of a colon (FIG. 4).

Generally, the contact plates 27 are disposed along the outer edges of the hood 25 since this edge generally forms the impact points for the end of the fiberscope 12.

Referring to FIG. 3, the control means 29 is suitably connected to the control unit 15, and particularly to the control knob 17, 18 to actuate the control unit 15 in response to a received signal from the tactile control device 10 in order to direct the distal end 11 of the fiberscope 12 in a direction opposite to the flexed hood section. The control means has a second circuit as well as a motorized component in this circuit for actuating the control knobs 17, 18.

The contact wires 28 and the control means 29 may also be connected to a display board 30 having indicators 21 such as lights to indicate the position of a flexed hood section relative to the remainder of the hood 25. Thus, the operator may bend the distal end 11 of the fiberscope 12 in accordance with the information received from the display board 30 or the distal end 11 may be automatically bent via the control means 29.

Referring to FIG. 4, the control wires 28 of the tactile control device may extend along the outside of the central flexible shaft 22 of the fiberscope 12 and be covered over by a sheath 36 which usually surrounds the tube 13 of the fiberscope. Such a protective sheath 36 is sufficient to protect the fiberscope 12 from the fluids and the like found in the colon. The sheath 36 should also be made of a material which is suitable for use in the colon.

Referring to FIG. 4, when in use, the fiberscope 12 is inserted into the colon 33 and travels along the passageway 34 formed by the colon 33. During this time, the operator can view the interior of the colon 33 via the viewing and illuminating system 14 (FIG. 1). Should a section of the hood 25 contact the wall of the colon 33, the contact pressure flexes the hood section inwardly. This, in turn, causes the contact plates 27 thereat to come into contact and complete the circuit along the associated wires 28. A suitable signal is then emitted to the control board 30 to indicate the area of pressure. This is represented by the appropriate panel indicator 31. Thus, the direction of the pressure point of maximum impact on an obstruction is indicated. In addition, the signal also activates the control means 29 such that the motorized component of the control means 29 is activated to turn the appropriate knob or knobs 17, 18 of the control unit 15 in the direction required to move the distal end 11 and thus, the hood 25, away from the point of pressure.

With the tactile control device 10 in operation, the fiberscope 12 will automatically seek the most central position within the colon 33 or within the lumen of an intestine or any other tedious structure. This facilitates passage and prevents impedance of the fiberscope.

It is to be noted that visual inspection of an internal organ occurs through the optic fiber bundle 19 in known manner. For example, a light source (not shown) projects light via a suitable means in the control unit 15 into and through some of the optic fibers to illuminate the object of interest. The lens 21 at the distal end 11 collects the reflected light from the object and transmits the reflected image through the remaining optic fibers to the eye-piece 20 or a viewing screen for visual examination by an operator.

Referring to FIG. 4, the tactile control device 10 may also include a plurality of pressure-sensitive contacts 35 which are disposed along the insertion tube 13 beneath a layer or sheath 36 of Dynacon or other suitable material with variable conductivity. These contacts 35 beneath the outer sheath 36 form a network of sensors which are able to emit warning signals when a given pressure is exceeded; thus warning the operator of impending disruption of the bowel by any portion of the instrument. As indicated, the contacts 35 may be disposed under the sheath 36 to generate signals to indicate that the sheath 36 is in contact with a bend in the colon passageway 34 with sufficient pressure that the tensile strength of the colon wall is in danger of being exceeded. Thus, excess pressure registered e.g. by an ohmmeter from contact 35 will signal the operator to cease the application of pressure to the colonoscope until the tube 13 can be reoriented to reduce the pressure against the colon wall. In this regard, the generated signal can be emitted via a suitable electrical circuit to the control board 30 to sound an audible warning signal and/or to give a visual warning signal.

Referring to FIG. 5, instead of using a flexible sheath with multiple contacts as the pressure sensitive devices, a series of pressure-sensitive microswitches 37 can be spaced along the tube 13 of a fiberscope under the flexible outer sheath 32. As shown, each microswitch 37 is of a suitable known construction, e.g. employing a movable button 38 which can be depressed into a housing 39 to close the switch and complete a circuit. For this purpose, a flexible plate 40 is positioned above each microswitch 37 to close the circuit should the tube 13 be subjected to undue pressure at the location. Each microswitch 37 is also connected to a positive wire 41 to emit a signal to the control board (not shown) as above, to inform the operator of an excess pressure condition at the location of the activated microswitch.

It is noted that the microswitches 37 are mounted not only along the tube 13 but also circumferentially about the tube 13. Further, the plates 40 are arranged to press radially inwardly relative to the tube axis.

Referring to FIG. 6, the pressure sensitive devices may also be in the form of micro dip switches 42 disposed at intervals along the tube 13.

Referring to FIG. 7, wherein like reference characters indicate like parts as above, the sensing devices 26 may also be in the form of microswitches as in FIGS. 5 and 6 rather than in the form illustrated in FIG. 1. Further, when used with pressure sensitive devices along the length of the tube of a fiberscope, the microswitches at the distal end are more sensitive than the sets of proximal switches. Thus, the distal microswitches are used for sensitive tip control while the other switches are used to prevent disruption of a structure, such as a colon.

This invention thus provides a tactile control device which can be easily incorporated into existing fiberscopes, particularly colonoscopes. In essence, the invention provides a remote sensing device which can be used to sense obstructions and to indicate such. An operator can the note the obstruction and visually adjust the fiberscope to avoid the obstruction or the control device may be interconnected with a system which automatically corrects the position of the distal end of a fiberscope to avoid a sensed obstruction and maneuvers the instrument to the center of a lumen by seeking the point of least resistance. Still further, the invention provides a tactile control device which can be used industrially to visually inspect objects which are relatively inaccessible.

What is claimed is:

1. In combination with a fiberscope including an elongated flexible insertion tube, an illuminating and viewing system mounted at a distal end of said tube and a control unit for bending said tube at said distal end in two planes;
   a tactile control device including
   a flexible hood circumferentially surrounding said illuminating and viewing system at said distal end, said hood projecting forwardly of said distal end; and
   a plurality of sensing devices disposed circumferentially on said hood forward of said distal end, said sensing devices being responsive to an inward flexing of said hood to emit a signal indicative of the location of a flexed section of said hood.

2. The combination as set forth in claim 1 wherein each sensing device includes a pair of electrically conductive plates disposed in slightly spaced relation to each other and a pair of contact wires, each said wire extending from a respective one of said plates whereby upon flexing of a section of said hood, said plates therein contact with each other to complete an electrical circuit through said wires and emit said signal.

3. The combination as set forth in claim 2 which further comprises a control means connected to each said pair of wires and to said control unit of said fiberscope to activate said control unit in response to a received signal to direct said distal end in a direction opposite said flexed hood section.

4. The combination as set forth in claim 2 wherein said sensing devices include contact points inside a pressure-sensitive digital foam sheath and which further comprises an ohmmetric resistance measuring device connected to said contact points for converting said signal into an indication of pressure.

5. The combination as set forth in claim 2 wherein said plates are piezoelectric crystals.

6. The combination as set forth in claim 2 wherein said plates are microspring sensors.

7. The combination as set forth in claim 2 which further comprises a display board having indicators thereon to indicate the position of a flexed hood section relative to the remainder of said hood.

8. In combination with a fiberscope including a distal end, a flexible optic fiber means extending to said distal end to transmit light thereto, a lens at said distal end, an eyepiece at a proximal end to view an image through said lens, and a control unit for remotely bending said distal end;
   a tactile control means comprising a flexible hood surrounding said distal end and projecting forwardly of said distal end, a plurality of sensing devices in said hood forward of said distal end to signal when a section of said flexible hood flexes upon contact with an obstruction.

9. The combination as set forth in claim 8 which further comprises a position display means to receive said signals from said sensing devices and to display signals in response thereto to an operator.

10. The combination as set forth in claim 8 wherein said sensing devices are contacts inside a pressure sensitive digital foam sheath.

11. The combination as set forth in claim 8 wherein said sensing devices are piezoelectric crystals.

12. The combination as set forth in claim 8 wherein said sensing devices are microspring sensors.

13. A tactile control device comprising
   a flexible spherical hood for mounting on a distal end of a flexible tube, and
   a plurality of pressure-sensitive sensing devices mounted in said hood, each said sensing device being responsive to an inward flexing of said hood for emitting a signal indicative of the location of a flexed section of said hood.

14. A tactile control device as set forth in claim 13 wherein said hood is a ball and said sensing devices are disposed circumferentially on said ball without fibroptic visualization.

15. A combination as set forth in claim 14 wherein said sensing devices are recessed within said ball.

16. In combination with a fiberscope including an elongated flexible insertion tube, an illuminating and viewing system mounted at a distal end of said tube and a control unit for bending said tube at said distal end in two planes;
   a tactile control device including a flexible hood about said distal end, and a plurality of pressure-sensitive sensing devices disposed circumferentially on said hood, each said device being responsive to flexing of said hood to emit a signal indicative of the location of a flexed section of said hood.

17. The combination as set forth in claim 16 wherein said tactile control device further includes a plurality of pressure-sensitive devices disposed along said insertion tube for emitting a signal in response to predetermined contact pressures on said tube at the locations of said devices.

18. The combination as set forth in claim 17 wherein said pressure-sensitive devices are flexible tubes.

19. The combination as set forth in claim 17 wherein said pressure-sensitive devices are microswitches.

20. The combination as set forth in claim 17 wherein said pressure-sensitive devices include a plurality of contacts within an outer sheath of flexible pressure digital foam and which further comprises an ohmmeter connected to said contacts to reflect changes in pressure by variations in electrical conductivity.

* * * * *

UNITED STATES PATENT AND TRADEMARK OFFICE
CERTIFICATE OF CORRECTION

PATENT NO. : 4,469,091
DATED : September 4, 1984
INVENTOR(S) : Charles A. Slanetz It is certified that error appears in the above-identified patent and that said Letters Patent is hereby corrected as shown below:

| Column | Line | From | To |
|--------|------|------|----|
| 5 | 61 | 21 | 31 |

Signed and Sealed this

Twelfth Day of February 1985

[SEAL]

Attest:

DONALD J. QUIGG

Attesting Officer    Acting Commissioner of Patents and Trademarks